US006635266B2

(12) United States Patent  
Messina

(10) Patent No.: US 6,635,266 B2  
(45) Date of Patent: *Oct. 21, 2003

(54) ANIMAL REPELLENT AND METHOD

(76) Inventor: James Messina, 58 Califon Rd., Long Valley, NJ (US) 07853

(*) Notice: Subject to any disclaimer, the term of this patent is extended or adjusted under 35 U.S.C. 154(b) by 0 days.

This patent is subject to a terminal disclaimer.

(21) Appl. No.: 10/044,201

(22) Filed: Jan. 12, 2002

(65) Prior Publication Data

US 2002/0110576 A1 Aug. 15, 2002

Related U.S. Application Data

(63) Continuation-in-part of application No. 09/783,625, filed on Feb. 14, 2001, now Pat. No. 6,383,508.

(51) Int. Cl.$^7$ ............................................... A01N 25/34
(52) U.S. Cl. ....................... 424/411; 424/405; 424/406; 424/407; 424/418; 424/421; 514/920
(58) Field of Search .................................. 424/411, 406, 424/405, 407, 418, 421, 747, 720; 514/920

(56) References Cited

U.S. PATENT DOCUMENTS

| 5,716,602 A | * | 2/1998 | Uick | 424/59 |
| 6,372,240 B1 | * | 4/2002 | Messina | 424/405 |
| 6,383,508 B1 | * | 5/2002 | Messina | 424/411 |

FOREIGN PATENT DOCUMENTS

| WO | 9102534 | * | 3/1991 |

* cited by examiner

*Primary Examiner*—Jean C. Witz
(74) *Attorney, Agent, or Firm*—Graham, Curtin & Sheridan; Richard T. Laughlin, Esq.

(57) ABSTRACT

An animal repellent formulation particularly suited to deer and geese, and a method for warding off the animals from a vegetated area. The formulation is an admixture of water, Rosemary oil emulsion and mint oil emulsion. Additional agents can be added, such as a thickener, white distilled vinegar, salt and dry eggs. The formulation can be applied to a support medium, such as clay or a length of rope, and then associated with the vegetation to be protected. The formulation can also be formed into a viscous composition and used in containers near the vegetation to be protected.

31 Claims, No Drawings

ANIMAL REPELLENT AND METHOD

The invention generally relates to an animal repellent and, in particular, the invention relates to a such a repellent composition which is transparent and can be applied to a wide range of surfaces and to a method for the use of such a composition.

This application is a continuation-in-part of U.S. patent application Ser. No. 09/783,625 filed Feb. 14, 2001 now U.S. Pat. No. 6,383,508.

BACKGROUND OF THE INVENTION

The prior art deer repellent formulation is described in U.S. Pat. No. 4,965,070, issued Oct. 23, 1990 to the same inventor as this application. The prior art formulation consisted essentially of, by volume, 68 to 90% water; 6 to 10% thiram; 0.5 to 2% chicken eggs; 1 to 2% liquid hot sauce; 2 to 16% adhesive to aid in adhering to vegetation; and 0.5 to 2% coloring dye. The dye is necessary so the coating will blend in with the foliage. There is no indication that such formulas can be used as a geese deterrent.

One problem of the prior art deer repellent formulation is that, although the ingredients are common materials, it requires approval of the Environmental Protection Agency ("EPA") which involves long and costly tests. Formulations of this type are applied by small companies, such as landscape gardeners, and the obtaining of approval from the EPA is financially prohibitive. This results in widespread destruction of homeowners' landscaping because of the unfettered proliferation of deer in suburban areas. Further, the prior art materials have a limited effective life and the odor of the formulation can limit its acceptance. A further problem with the prior art compositions is that a colorant to hide their presence on the foliage is usually necessary.

OBJECTS OF THE INVENTION

One object of the present invention is to provide an improved animal repellent formulation for application to a shrub, plant or the like which can be acceptable under EPA regulations.

Another object of the invention is to provide an animal repellent formulation more acceptable to humans.

Another object of the invention is to make use of EPA-approved components without reduction of the effectiveness of the treatment.

A still further object is to provide such a composition which is transparent.

Other objects and the advantages of the invention will appear from the following description.

SUMMARY OF THE INVENTION

According to the present invention, a non-toxic animal repellent formulation, not subject to EPA approval and particularly applicable to deer and geese, and method for its use are provided. The key part of the formulation is the use of a combination of rosemary oil and mint oil in an aqueous mixture. The composition is usually prepared in a concentrate which is diluted with water on the job site to reduce transportation costs. A typical effective mixture for deer would be one gallon of concentrate to approximately 10 gallons of water. Since the preferred method of application is by spraying the concentration in a given area, the actual amount applied depends on the operator and the dilution. A preferred application would be one gallon of the diluted concentrate per 4,000 square feet of surface area in a fine spray. Water should not be applied to the treated area for at least 20 minutes after application.

In the preferred concentrate composition, about 5 to 20 ounce of Rosemary oil emulsion is admixed with 5 to 20 ounces of mint oil emulsion. A conventional thickener, such as zanthan gum, can be added to produce the optimum viscosity for spraying and handling. Typical would be 1 to 5% of the total composition of thickener. All of the percentages are by volume of the composition. The mixture is added to form a gallon (128 ounces) of concentrate. If desired, the formulation can be modified by adding other components conventionally found in animal repellent. The addition of table salt of about 1 to 15 teaspoonfuls is desirable. Further, 10 to 30 ounces of white distilled vinegar can be added. About 10 to 30 ounces of dry, raw eggs can also be added.

As indicated, prior to application to vegetation, the composition is diluted in a concentration of one part of repellent concentrate to approximately 5 to 15 parts water. The mixture is stirred until a uniform composition is obtained. The composition is sprayed with a fine nozzle power spray producing a fine mist on the foliage to be protected in about one gallon for each 4,000 square feet of foliage.

As a general rule, a concentration of five times the concentration of effective components for deer is required for geese.

As an alternate procedure, the composition can be impregnated into or coated onto a material such as a rope with the rope being placed around the vegetation to be protected. As another alternative, the composition can be left in containers which are distributed in a uniform manner around the area being treated.

DESCRIPTION OF THE PREFERRED EMBODIMENT

The preferred deer repellent formulation is an aqueous solution or mixture of water and a composition comprising 10 ounces of rosemary oil emulsion, 10 ounces of mint oil emulsion, zanthan gum as a thickener and sufficient water to make one gallon (128 ounces). If desired, the formulation can be modified by adding 20 ounces of white distilled vinegar, 20 ounces of dry eggs and 10 teaspoons of table salt. In certain instances, when weather conditions are dry, a preservative such as potassium sorbate can be used. The thickener can be added to give the composition the desired application characteristics. Typical would be 1 to 5% of the total composition of thickener. All of the percentages are by volume of the composition. In some instances where greater adherence to the foliage is desired, a sticker such as the material sold under the trademark "Nu Film P" can be added. As an alternative, "CLEARSPRAY" or the like can be used. In particular, the adhesive is used for a deer repellent assembly, which is exposed to substantial amounts of rain or snow.

The composition of the invention can be utilized in the manner described in U.S. Pat. No. 5,183,661 issued on Feb. 2, 1993 to James Messina. The formulation of the invention can be applied to a support medium such as a solid braid, number 8, cotton and polyester, one-quarter inch diameter, sash cord rope of 100 foot length, which is sold by the Lehigh Group, Allentown, Pa. 18105, U.S.A. The support medium can also be a clay material, which ranges in size of clay granules or particles, from dustless fine granules to about one-quarter inch overall diameter or thickness granules. The clay material comes packaged in a 0.20 pound bag, which is made of a finely woven cloth material and which has a drawstring along an open top edge thereof, and which has a size of about 4 inches in height by about 3 inches in width when flat. The drawstring threads through spaced holes located about one-half inch down from the bag top edge.

The animal repellent assembly of support rope and formulation can be wrapped around a shrub or plant or strung between shrubs and plants. The deer repellent assembly of support medium clay material and formulation can be distributed under and around shrubs and plants or the like.

It is noted that 16 fluid ounces of the repellent formulation is sufficient to wet the 100 foot length of one-quarter inch diameter rope. Also, 11 fluid ounces of animal repellent formulation is sufficient to wet throughout the one pound of clay granules. A shorter rope length requires proportionally less fluid ounces of formulation based upon rope length and rope cross section areas. Less than one pound of clay granules medium requires proportionally less fluid ounces of formulation based upon medium volume.

The animal repellent formulation can also be prepared for addition to a container having sufficient holes or openings to allow the deer to lick the container and come in contact with the repellent formulation. The fluid deer repellent formulation is admixed with wheat flower and corn cob grounds to form a semi-solid composition and then poured into the container having openings.

The following examples are given for purposes of illustration and not by way of limitation.

EXAMPLE 1

The deer repellent formulation in the preferred embodiment for outdoor application as follows:
- 7.56 grams of rosemary oil emulsion
- 5.04 grams of mint oil emulsion Water is added to make one gallon of mixture to make a concentrate which can be diluted with water on the job site and applied to the foliage in a fine mist from a power spray.

EXAMPLE 2

The deer repellent formulation of Example 1 can have added:
- 9.1 grams of white distilled vinegar (30%)
- 11.12 grams of table salt
- 56.6 grams of dried chicken eggs
- 11.2 grams of zanthan gum Water is added to make one gallon of mixture to make a concentrate which can be diluted with water on the job site and applied to the foliage in a fine mist from a power spray.

EXAMPLE 3

The deer repellent formulation in the preferred embodiment for outdoor application as follows:
- 10 ounces of rosemary oil emulsion
- 10 ounces of mint oil emulsion Water is added to make one gallon of mixture to make a concentrate which can be diluted with water on the job site and applied to the foliage in a fine mist from a power spray.

EXAMPLE 4

The deer repellent formulation of Example 3 can have added:
- 20 ounces of white distilled vinegar (30%)
- 10 ounces of table salt
- 20 ounces of dried chicken eggs.

EXAMPLE 5

The deer repellent formulation of Example 4 with the addition of potassium sorbate as a preservative.

EXAMPLE 6

The deer repellent formulation of Example 4 with the addition of 1 to 10 ounce of zanthan gum as a thickener.

EXAMPLE 7

The deer repellent formulation of Example 4 with the addition of 5 ounce of "Nu-Film P" as a sticker to aid in the adherence of the formulation to the foliage.

EXAMPLE 8

The composition of Example 4 is formed into a solid medium by mixing the following:
- 2 cups of wheat flower
- 2 cups of ground up corn cobs
- 2 cups of the formula of Example 2

The composition is mixed uniformly and then added to a container with holes. The size of the container is 1 inch in diameter by 2 inch in length. The container is hung or tied to the plant to be protected or elevated on a post adjacent to the plant.

EXAMPLE 9

The deer repellent composition of Example 4 is utilized as follows:
- a 100 foot length of support rope of one-quarter inch diameter, and of cotton and polyester, solid braid material;
- 16 fluid ounces of deer repellent formulation of Example 2 is placed in a container. The deer repellent formulation is distributed evenly along the support rope length by dipping the rope into the container.

EXAMPLE 10

The deer repellent formulation of Example 3 is admixed as follows:
- one pound by weight of clay granules in a particle size distribution from dustless fine particles to about one-quarter inch overall thickness particles for a support medium; eleven fluid ounces of deer repellent formulation of Example 3.

The deer repellent formulation is mixed with the support medium clay granules.

EXAMPLE 11

The deer repellent formulation in the preferred embodiment for outdoor application as follows:
- 1.0 ounces of rosemary oil emulsion
- 1.0 ounces of mint oil emulsion
- 0.105 ounces of zanthan gum
- 1.25 pounds of dried eggs
- 1.0 ounces of table salt
- 3.36 ounces of white vinegar (30%)

Water is added to make one gallon of mixture to make a concentrate which can be diluted with water on the job site and applied to the foliage in a fine mist from a power spray.

EXAMPLE 12

The deer repellent formulation in the preferred embodiment for outdoor application as follows:
- 1.5 ounces of rosemary oil emulsion
- 1.0 ounces of mint oil emulsion
- 0.325 ounces of zanthan gum
- 1.25 pounds of dried eggs
- 1.0 ounces of table salt
- 3.36 ounces of white vinegar (30%)
- 5.0 ounces of kaolin clay (as sticking agent)

Water is added to make one gallon of mixture to make a concentrate which can be diluted with water on the job site and applied to the foliage in a fine mist from a power spray.

EXAMPLE 13

A repellent formulation particularly applicable to geese is as follows:
- 10.0 ounces of rosemary oil emulsion
- 10.0 ounces of mint oil emulsion
- 0.325 ounces of zanthan gum
- 1.25 pounds of dried eggs
- 1.0 ounces of table salt
- 3.36 ounces of white vinegar (30%)
- 5.0 ounces of kaolin clay (as sticking agent)

Water is added to make one gallon of mixture to make a concentrate which can be diluted with water on the job site and applied to the foliage in a fine mist from a power spray.

While the invention has been described in its preferred embodiment, it is to be understood that the words which have been used are words of description rather than limitation and that changes may be made within the purview of the appended claims without departing from the true scope and spirit of the invention in its broader aspects.

What is claimed is:

1. An animal repellent concentrate particularly suited to repel deer comprising an aqueous mixture of 5 to 10 ounces of rosemary oil emulsion, 5 to 20 ounces of mint oil emulsion, 10 to 30 ounces of dry eggs, and sufficient water to make approximately 128 ounces of concentrate.

2. The animal repellent concentrate as defined in claim 1 with the addition of a thickening agent to increase the viscosity of the mixture.

3. The animal repellent concentrate as defined in claim 2 wherein the thickening agent is xanthan gum.

4. The animal repellent concentrate as defined in claim 1 containing in addition 10 to 30 ounces of white distilled vinegar.

5. The animal repellent concentrate as defined in claim 1 with the addition of 1 to 15 teaspoons of table salt.

6. The animal repellent concentrate as defined in claim 1 wherein the concentrate is applied to a carrier to be distributed in the area desired to repel the animals.

7. The animal repellent as defined in claim 6 wherein the carrier is a rope and about 16 fluid ounces of the concentrate is evenly applied to the rope.

8. The animal repellent as defined in claim 7 wherein the carrier rope is about one-quarter inch in diameter and made of cotton, polyester or a combination of cotton and polyester.

9. The animal repellent as defined in claim 6 wherein the carrier is a canister open to the air.

10. The animal repellent as defined in claim 1 wherein approximately one pound by weight of clay granules is added to the concentrate mixture, the clay granules having a particle size distribution from about dustless fine particles to about one-quarter inch.

11. An animal repellent as defined in claim 10 wherein a selected volume of repellent formation of about eleven fluid ounces of formulation per pound of support medium of clay granules, said formulation being about evenly distributed throughout the support medium of clay particles.

12. The animal repellent concentrate as defined in claim 1 wherein the animal is deer.

13. The animal repellent concentrate as defined in claim 1 wherein the animal is geese.

14. The animal repellent concentrate as defined in claim 2 wherein the animal is deer.

15. The animal repellent concentrate as defined in claim 2 wherein the animal is geese.

16. The animal repellent concentrate as defined in claim 3 wherein the animal is deer.

17. The animal repellent concentrate as defined in claim 3 wherein the animal is geese.

18. The animal repellent concentrate as defined in claim 4 wherein the animal is deer.

19. The animal repellent concentrate as defined in claim 4 wherein the animal is geese.

20. The animal repellent concentrate as defined in claim 5 wherein the animal is deer.

21. The animal repellent concentrate as defined in claim 5 wherein the animal is geese.

22. The animal repellent concentrate as defined in claim 6 wherein the animal is deer.

23. The animal repellent concentrate as defined in claim 6 wherein the animal is geese.

24. An animal repellent concentrate particularly suited to repel deer and geese comprising an aqueous mixture of 7.56 grams of rosemary oil emulsion, 5.04 grams of mint oil emulsion, a thickening agent to control viscosity, 9.1 grams of white distilled vinegar, 56.6 grams of dry eggs, 11.12 grams of sodium chloride and sufficient water to make approximately one gallon of concentrate.

25. A animal repellent concentrate particularly suited to repel deer and geese comprising an aqueous mixture of 1.0 ounces of rosemary oil emulsion, 1.0 ounces of mint oil emulsion, a thickening agent to control viscosity, 3.36 ounces of white distilled vinegar, 1.25 pounds of dry eggs, 1.0 ounces of table salt and sufficient water to make one gallon of concentrate.

26. A animal repellent concentrate particularly suited to repel deer and geese comprising an aqueous mixture of 1.5 ounces of rosemary oil emulsion, 1.0 ounces of mint oil emulsion, a thickening agent to control viscosity, 3.3 ounces of white distilled vinegar, 1.25 pounds of dry eggs, 1.0 ounces of table salt, 5.0 ounces of kaolin clay and sufficient water to make one gallon of concentrate.

27. A animal repellent concentrate particularly suited to repel deer and geese comprising an aqueous mixture of 5.0 ounces of rosemary oil emulsion, 5.0 ounces of mint oil emulsion, a thickening agent to control viscosity, 3.3 ounces of white distilled vinegar, 1.25 pounds of dry eggs, 1.0 ounces of table salt, 5.0 ounces of kaolin clay and sufficient water to make one gallon of concentrate.

28. A animal repellent concentrate particularly suited to repel deer and geese comprising an aqueous mixture of 5 to 20 ounce of rosemary oil emulsion, 5 to 20 ounces of mint oil emulsion, a thickening agent to control viscosity, 10 to 30 ounces of white distilled vinegar, 10 to 30 ounces of dry eggs, 1 to 15 tablespoons of table salt and sufficient water to make approximate 128 ounces of concentrate.

29. A method of repelling deer or geese from an area of vegetation, including the steps of: preparing the animal repellent formulation as defined in claim 1 and applying to the vegetation a mixture of about one part concentrate to about 8 to 12 parts water.

30. The method of claim 24, wherein the mixture is applied to a support medium braided rope of about one-quarter inch in diameter.

31. The method of claim 25, wherein the support medium is a volume of clay granules having a particle size distribution from dustless fine particles to about one-quarter inch thickness particles.

* * * * *

UNITED STATES PATENT AND TRADEMARK OFFICE
CERTIFICATE OF CORRECTION

PATENT NO.    : 6,635,266 B2
DATED         : October 21, 2003
INVENTOR(S)   : James Messina It is certified that error appears in the above-identified patent and that said Letters Patent is hereby corrected as shown below:

<u>Column 5,</u>
Lines 37-41, Claim 1, should read as follows:
1. An animal repellent concentrate particularly suited to repel deer and geese comprising an aqueous mixture of 5 to 20 ounces of rosemary oil emulsion, 5 to 20 ounces of mint oil emulsion, 10 to 30 ounces of dry eggs, and sufficient water to make approximately 128 ounces of concentrate.

Signed and Sealed this

Eleventh Day of May, 2004

JON W. DUDAS
*Acting Director of the United States Patent and Trademark Office*